United States Patent [19]

Archibald

[11] 4,410,322

[45] * Oct. 18, 1983

[54] NONPULSATING TV PUMP AND DISPOSABLE PUMP CHAMBER

[75] Inventor: G. Kent Archibald, St. Paul, Minn.

[73] Assignee: AVI, Inc., St. Paul, Minn.

[*] Notice: The portion of the term of this patent subsequent to Dec. 2, 1997 has been disclaimed.

[21] Appl. No.: 186,148

[22] Filed: Sep. 10, 1980

Related U.S. Application Data

[62] Division of Ser. No. 19,223, Mar. 9, 1979, Pat. No. 4,236,880.

[51] Int. Cl.³ .............................................. A61M 5/00
[52] U.S. Cl. .................................. 604/153; 92/98 D; 417/478; 138/30
[58] Field of Search ................ 417/63, 474, 478, 479, 417/480, 510, 244; 92/98 D, 92; 128/214 F; 138/30, 26; 604/153, 118

[56] References Cited

U.S. PATENT DOCUMENTS

| | | |
|---|---|---|
| 1,085,818 | 2/1914 | Oxnard . |
| 1,615,140 | 1/1927 | Rusdell . |
| 1,676,114 | 7/1928 | Rusdell . |
| 2,017,974 | 10/1935 | Kastner .......................... 417/510 X |
| 2,017,974 | 10/1935 | Kastner .............................. 417/510 |
| 2,328,406 | 8/1943 | Atchisen .............................. 138/30 |
| 2,703,084 | 3/1955 | Tomlinson . |
| 2,925,814 | 2/1960 | Vibber et al. ...................... 128/214 |
| 3,044,655 | 7/1962 | Anderson et al. .................. 128/230 |
| 3,050,004 | 4/1962 | Heintzmann ......................... 417/63 |
| 3,051,530 | 8/1962 | Ayers, Jr. ............................... 303/6 |
| 3,091,239 | 5/1963 | Moeller ................................ 128/214 |
| 3,114,257 | 12/1963 | Foster et al. .......................... 73/45.5 |
| 3,143,969 | 8/1964 | Eames et al. ...................... 417/63 X |
| 3,180,235 | 4/1965 | Schmitz ..................................... 92/95 |
| 3,198,385 | 8/1965 | Maxwell ............................... 222/41 |
| 3,199,511 | 8/1965 | Kulick .................................. 128/214 |
| 3,227,092 | 1/1966 | Clark ..................................... 417/475 |
| 3,295,458 | 1/1967 | Steffes .................................. 103/150 |
| 3,314,594 | 4/1967 | Rietdijk .......................... 417/244 X |
| 3,335,724 | 8/1967 | Gienapp .............................. 128/218 |
| 3,339,464 | 9/1967 | Rietdijk ................................. 92/98 |
| 3,359,910 | 12/1967 | Latham ................................ 417/478 |
| 3,372,624 | 3/1968 | Rietdijk ..................................... 92/84 |
| 3,375,759 | 4/1968 | Smith ........................................ 92/98 |
| 3,384,080 | 5/1968 | Muller ................................... 128/214 |
| 3,391,644 | 7/1968 | Taplin ................................... 103/150 |
| 3,410,779 | 11/1968 | Whitehead, Jr. et al. .......... 204/195 |
| 3,423,939 | 1/1969 | Lewis et al. ......................... 92/98 D |
| 3,428,042 | 2/1969 | Chesnut ................................... 128/1 |
| 3,451,393 | 6/1969 | Sarnoff ................................. 128/214 |
| 3,464,359 | 9/1969 | King et al. ............................ 103/38 |
| 3,488,763 | 1/1970 | Lofquist, Jr. ........................ 103/150 |
| 3,559,644 | 2/1971 | Stoft ..................................... 128/214 |
| 3,640,276 | 2/1972 | Dancy, Jr. . |
| 3,640,277 | 2/1972 | Adelberg . |
| 3,648,694 | 3/1972 | Mogos et al. . |
| 3,670,926 | 6/1972 | Hill . |
| 3,690,318 | 9/1972 | Gersuch . |
| 3,704,080 | 11/1972 | Cross . |
| 3,730,495 | 5/1973 | Elam . |
| 3,730,650 | 5/1973 | Kling .................................... 417/475 |
| 3,731,679 | 5/1973 | Wilhelmson et al. . |
| 3,731,680 | 5/1973 | Wright et al. . |
| 3,737,251 | 6/1973 | Berman et al. ......................... 417/12 |
| 3,762,280 | 10/1973 | Kreuter et al. . |
| 3,769,879 | 11/1973 | Lofquist, Jr. . |
| 3,798,982 | 3/1974 | Lundquist . |
| 3,809,498 | 5/1974 | Lewis et al. ........................... 417/63 |
| 3,809,507 | 5/1974 | Baglai . |
| 3,810,719 | 5/1974 | Wolthers . |
| 3,811,800 | 5/1974 | Shill ..................................... 417/479 |
| 3,874,826 | 4/1975 | Lundquist et al. . |
| 3,884,228 | 5/1975 | Hahn . |
| 3,886,938 | 6/1975 | Szabo et al. . |
| 3,888,239 | 6/1975 | Rubinstein . |
| 3,894,538 | 7/1975 | Richter . |
| 3,895,631 | 7/1975 | Buckles et al. . |
| 3,895,741 | 7/1975 | Nugent . |
| 3,901,231 | 8/1975 | Olsen ............................... 128/214 F |
| 3,923,060 | 12/1975 | Ellinwood, Jr. . |
| 3,934,480 | 1/1976 | Nederlof . |
| 3,948,589 | 4/1976 | Dubois . |
| 3,963,024 | 6/1976 | Goldowsky . |
| 3,969,991 | 7/1976 | Comstock et al. . |
| 3,985,133 | 10/1976 | Jenkins et al. . |
| 3,993,061 | 11/1976 | O'Leary . |
| 3,993,065 | 11/1976 | Szabo et al. . |
| 3,993,069 | 11/1976 | Buckles et al. . |
| 3,994,294 | 11/1976 | Knute . |
| 4,012,173 | 3/1977 | Everson, Jr. . |
| 4,029,094 | 6/1977 | Winicki . |
| 4,030,495 | 6/1977 | Virag . |

| | | |
|---|---|---|
| 4,037,598 | 7/1977 | Georgi . |
| 4,039,269 | 8/1977 | Pickering .......................... 417/510 |
| 4,048,474 | 9/1977 | Olesen . |
| 4,056,043 | 11/1977 | Sriramamurty et al. . |
| 4,063,551 | 12/1977 | Sweeney . |
| 4,065,230 | 12/1977 | Gezari . |
| 4,067,332 | 1/1978 | O'Leary . |
| 4,067,334 | 1/1978 | Haller . |
| 4,070,746 | 1/1978 | Sandvik et al. . |
| 4,079,737 | 3/1978 | Miller . |
| 4,094,318 | 6/1978 | Burke et al. . |
| 4,101,057 | 7/1978 | LoMaglio .......................... 417/479 |
| 4,105,028 | 8/1978 | Sadlier et al. . |
| 4,117,727 | 10/1978 | Friswell et al. . |
| 4,121,584 | 10/1978 | Turner et al. . |
| 4,136,692 | 1/1979 | Goldowsky . |
| 4,136,693 | 1/1979 | Dyke . |
| 4,137,913 | 2/1979 | Georgi . |
| 4,137,915 | 2/1979 | Kamen . |
| 4,137,940 | 2/1979 | Faisandier . |
| 4,142,524 | 3/1979 | Jassawalla et al. . |
| 4,236,880 | 12/1980 | Archibald .......................... 417/478 |

*Primary Examiner*—Richard E. Gluck
*Attorney, Agent, or Firm*—Kinney, Lange, Braddock, Westman and Fairbairn

[57] ABSTRACT

A small, accurate, reliable and economical pump which is particularly useful in intravenous (IV) feeding includes a disposable pump chamber and a pump housing. The disposable pump chamber has an inlet, an outlet, and first and second flexible rolling diaphragm pumping chambers. First and second cylinders in the pump housing are positioned to eceive the first and second flexible rolling diaphragms of the disposable pump chamber. First and second pistons are movable in the first and second cylinders, respectively. In addition, first and second valves are provided in the pump housing. The first valve controls fluid flow between the inlet and the first flexible rolling diaphragm pump chamber, while the second valve controls fluid flow between the first flexible rolling diaphragm pumping chamber and the second flexible rolling diaphragm pumping chamber. A motor and cam shaft drive the first and second pistons and the first and second valves. The fist and second valves are controlled so that one valve is closed at all times, thereby providing fail safe operation of the pump.

11 Claims, 22 Drawing Figures

NONPULSATING IV PUMP AND DISPOSABLE PUMP CHAMBER

This is a division of application Ser. No. 19,223 filed Mar. 9, 1979 now U.S. Pat. No. 4,236,880.

BACKGROUND OF THE INVENTION

1. Field of the Invention

The present invention relates to pumping apparatus. In particular, the present invention relates to volumetric infusion pumps for administration of intravenous (IV) fluids.

2. Description of the Prior Art

To improve health care, there has been considerable effort with regard to the administration of intravenous (IV) fluid. For many years IV solutions were administered only by the force of gravity. The volume rate was measured by counting the number of drops per minute. In many instances this method proved unsatisfactory. Drop size is directly proportional to surface tension, which is affected by viscosity, temperature, type of solution, and also drop size is affected by the speed at which the drop forms. The drop rate is affected by the gravitational force and the restrictions of the tube and needle. If a tube is partly occluded, the drop rate will decrease or as the IV supply decreases the hydrostatic pressure will decrease causing a decrease in drop rate. In many cases, therefore, the variability of both the drop size and the drop rate (both of which are for the most part beyond the control of the operator) makes this method of administration of intravenous fluid unsatisfactory.

Improvements have been made by adding an electronic drop counter together with either a controller or a peristaltic pump. The electronic drop counter and controller combination controls the drop rate but makes no improvements in controlling drop size, and also has the deficiency of not being able to control drop rate if back pressure increases beyond the hydrostatic forcing pressure. The electronic drop counter and peristaltic pump combination increases the forcing pressure but lacks an accurate metering method.

Improvement in metering methods results with the use of displacement pumps, which offer the capability of greater precision in controlling IV flow rates than is possible with the prior art IV controllers which depend on gravity. These pumps, in addition to metering the fluid, also apply positive pressure to the fluid or the IV tubing. The displacement pump can generally be categorized as peristaltic (such as described in U.S. Pat. No. 3,737,251 by Berman et al) or piston-cylinder (such as described in U.S. Pat. No. 3,985,133 by Jenkins et al) or pulsating (such as described in U.S. Pat. No. 3,874,826 by Lundquist).

The peristaltic pump, although generally an improvement over the prior art, has a number of disadvantages. First, the peristaltic action results in friction, which precludes administering whole blood because it causes damage to the blood cells. Second, the peristaltic action involves stretching an elastomer material, which may allow air to enter the IV solution. Third, stretching an elastomer material in a peristaltic manner does not lend itself to an efficient use of energy. Because of the ambulatory patient and possibility of a loss of power, a battery backup for the pump is required, and it is desirable therefore that the pump be as efficient as possible.

The piston-cylinder pumps of the prior art provide for accurate metering and positive pressure, but also have several disadvantages. First, because intravenous therapy requires that the pump maintain a germ-free barrier, and cost prohibits cleaning and sterilization after each use, the pumping chamber must be disposable and inexpensive to manufacture. This has been difficult to achieve with the prior art piston-cylinder pumps. To reduce manufacturing costs, some prior art pumps use only one chamber and two valves. This requires that the pump cycle have two parts, a fill, and an empty; therefore, IV therapy is interrupted during the fill portion of the cycle. Second, some of the prior art piston-cylinder pumps have difficulty meeting the requirements of providing reliable and germ-free seals against sliding surfaces. Third, the friction of a piston-cylinder pump is a cause for reduced efficiency.

The pulsating pumps provide a continuous pulsing flow, but also have significant disadvantages. First, the self-contained valving of these pumps has added to the complexity and expense of the disposable pump chamber. Second, the pulsing action against a spring load or an elastomer material does not lend itself to efficient operation.

U.S. Pat. No. 3,809,507 by Baglai describes a pump which is not intended specifically for use in IV therapy, but which does provide a continuous pulse-free flow. The valves in this pump are either located on moving parts or located at a fixed location and connected by a flexible tube. This approach does not lend itself to an economical disposable pump chamber as is required for IV applications. Also, without the valves biased or powered, the pump in the off condition may continue to supply fluid (i.e. it suffers from "siphoning"). This is an unsafe condition for IV therapy.

Another general problem with the prior art IV equipment is that no way is provided to select and sense the back pressure at which an alarm will sound. Therefore the patient, in case of an infiltration, is subjected to the maximum back pressure that the pump is able to supply. Often this pressure is beyond the safe limits for a particular patient or application.

SUMMARY OF THE INVENTION

The present invention is a small, accurate, reliable, and economical pump which is particularly useful in intravenous (IV) applications. The pump includes a disposable pump chamber and a pump housing. The disposable pump chamber has an inlet, an outlet, and first and second flexible rolling diaphragm pumping chambers.

The pump housing has first and second cylinders for receiving the first and second flexible rolling diaphragm pumping chambers. First and second pistons are movable in the first and second cylinders, respectively. First and second valve means are also provided to control fluid flow between the inlet and outlet of the disposable pump chamber. The first valve means controls fluid flow between the inlet and the first flexible rolling diaphragm pumping chamber, while the second valve means controls fluid flow between the first flexible rolling diaphragm pumping chamber and the second flexible rolling diaphragm pumping chamber. Drive means cause relative motion of the first cylinder and first piston and relative motion of the second cylinder and second piston to vary the volumes of the first and second flexible rolling diaphragm pumping chambers.

By proper selection of the volumes of the first and second flexible rolling diaphragms and the drive rates by which the volumes are varied, an essentially pulse-free output can be produced.

For intravenous feeding applications, it is important that siphoning does not occur when the pump is stopped for any reason. In the preferred embodiments, the present invention controls the first and second valves so that at least one valve is closed at all times. As a result, fail safe operation of the pump is achieved.

The present invention also preferably includes a third flexible diaphragm chamber between the second flexible rolling diaphragm pumping chamber and the outlet of the disposable pump chamber. Back pressure is sensed by movement of the third flexible rolling diaphragm chamber.

In the case of use in intravenous feeding, it is important to sense the presence of any air bubbles in the fluid being pumped. The present invention also preferably includes an air detection system which measures dielectric constant at two different positions of the disposable pump chamber as fluid is pumped. As air passes through the disposable pump chamber, the change in dielectric constants between the two locations is sensed, and an alarm is provided.

DETAILED DESCRIPTION OF THE PREFERRED EMBODIMENTS

Figure 1:
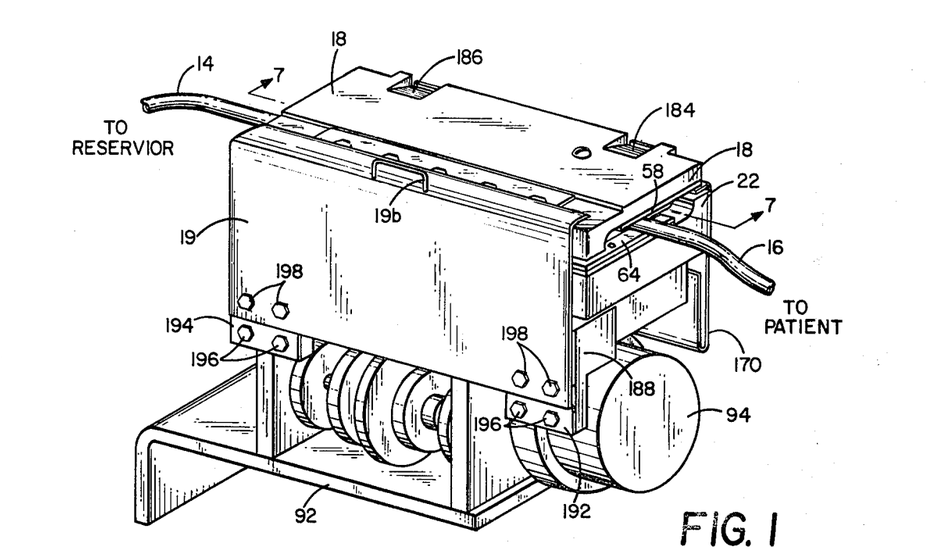
FIG. 1 is a perspective view of a preferred embodiment of the intravenous pump and disposable pump chamber of the present invention.
Figure 2:
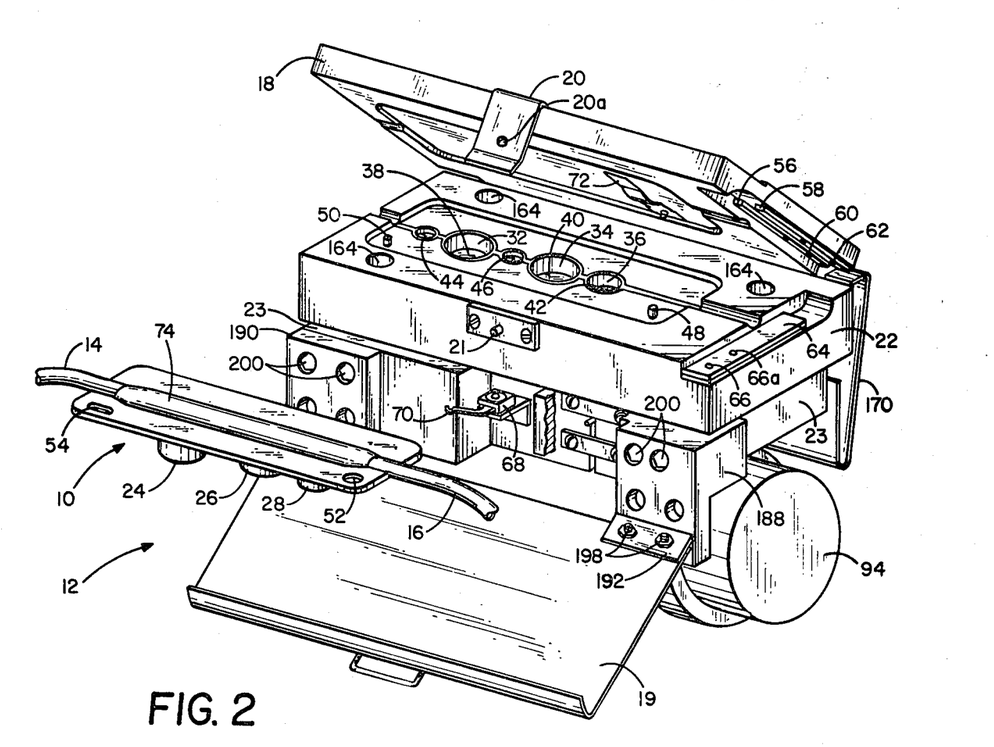
FIG. 2 is a perspective view of the IV pump and disposable pump chamber, with the pump housing open and the disposable pump chamber removed.

In FIGS. 1 and 2, perspective views of the IV pump of the present invention are shown. As illustrated in these figures, the IV pump does not include an outer housing which typically encloses a pump, as well as associated control circuitry. This outer housing has been removed and the control circuitry is not shown for the purpose of simplification of illustration.

The pump shown in FIGS. 1 and 2 includes disposable pump chamber 10 and housing 12. Inlet tubing 14 and outlet tubing 16 are connected at opposite ends of disposable pump chamber 10. Inlet tubing 14 is connected to a reservoir (not shown) of IV liquid, and outlet tubing 16 supplies the IV liquid from the pump to the patient (not shown).

In the preferred embodiments of the present invention, the IV pump is oriented in a vertical rather than a horizontal orientation as shown in FIGS. 1 and 2. The vertical orientation has inlet tubing 14 entering the pump at the bottom and outlet tubing 16 leaving the pump at the top. This orientation of the pump is preferred, since it prevents air from accumulating in the lines during the initial set-up and purging of the IV system.

IV therapy requires that the pump maintain a germ-free barrier. As a result, disposable pumping chamber 10 is used for one IV application and then discarded. Pump housing 12, on the other hand, does not physically contact the IV liquid, and may be reused many times. Pump housing 12 includes a hinged top cover 18 which may be open, as shown in FIG. 2, to permit insertion and removal of disposable pumping chamber 10.

Hinged latch 19 latches the pump in a closed, operative position. When hinged latch 19 is pulled downward, as shown in FIG. 2, top cover 18 may then be pivoted open by grasping latch 20. As shown in FIG. 2, latch 20 has a hole 20A which engages latch pin 21.

As shown in FIGS. 1 and 2, the pump housing 12 further includes a diaphragm enclosure 22 which, together with top cover 18, receives and holds disposable pump chamber 10. Underlying diaphragm enclosure 22 is cam housing 23, which supports the motor, cam shaft, and valve and piston rods of the IV pump.

In the preferred embodiments of the present invention, diaphragm enclosure 22 is spring mounted to cam housing 23, so that when latch 19 and latch 20 are both disconnected, diaphragm enclosure 22 moves away from cam housing 23. As will be discussed in further detail later, this ensures that all pistons and valves are sufficiently displaced from the top surface of diaphragm enclosure 22 so that disposable pump chamber 10 may be inserted regardless of the position of the valves and pistons in the particular pumping cycle.

As shown in FIG. 2, disposable pump chamber 10 contains three flexible rolling diaphragm chambers 24, 26, and 28 which protrude downward from the lower surface of disposable pumping chamber 10. Chambers 24 and 26 are first and second pumping chambers, respectively, while chamber 28 is a pressure monitoring chamber which moves in response to back pressure on the fluid passing from chamber 10 through outlet tubing 16.

In normal use, IV fluid is supplied through inlet tubing 14 to first rolling diaphragm pumping chamber 24. It is then pumped into second rolling diaphragm pumping chamber 26, through pressure sensing chamber 28, to outlet tubing 16 and from there to the patient. In the preferred embodiments of the present invention, first and second rolling diaphragm pumping chambers 24 and 26 are driven in such a manner that the output flow of IV fluid through outlet tubing 16 is essentially pulse-free and at an accurate controlled flow rate.

Diaphragm enclosure 22 includes first, second and third cylinders 32, 34, and 36 which receive the downwardly projecting rolling diaphragm chambers 24, 26, and 28, respectively, of disposable pump chamber 10. First piston 38 is movable within first cylinder 32 to vary the volume of rolling diaphragm pumping chamber 24. Similarly, second piston 40 is movable within second cylinder 34 to vary the volume of second flexible rolling diaphragm pumping chamber 26. Both first piston 38 and second piston 40 are motor driven, as will be discussed later. Unlike first and second pistons 38 and 40, third piston 42 is not motor driven, but rather is movable within third cylinder 36 in response to fluid pressure within pressure sensing chamber 28.

First and second valves 44 and 46 are also provided within diaphragm enclosure 22. First valve 44 is positioned between the end of inlet tubing 14 and first flexible diaphragm pumping chamber 24. First valve 44 is motor driven, and when in its uppermost position, pinches off the flexible portion of disposable pumping chamber 10 between inlet tubing 14 and first pumping chamber 24. When in its lowermost position, first valve 44 permits fluid flow from inlet tubing 14 to first pumping chamber 24.

Similarly, second valve 46 is positioned between first flexible diaphragm pumping chamber 24 and second flexible diaphragm pumping chamber 26. The second valve 46 is also motor driven, and when in its uppermost position, pinches off the flexible portion of disposable pumping chamber 10 between the first flexible; diaphragm pumping chamber 24 and second flexible diaphragm pumping chamber 26. When in its lowermost position, second valve 46 permits fluid flow from the first pumping chamber 24 to the second pumping chamber 26.

Also shown in FIG. 2 are alignment pins 48 and 50, which mate with alignment holes 52 and 54, respectively, in disposable pump chamber 10. Alignment pins 48 and 50, together with alignment holes 52 and 54, assure that disposable pump chamber 10 can be inserted into the pump housing 12 quickly and in only one orientation. Downwardly projecting rolling diaphragm chambers 24, 26 and 28 also provide alignment; therefore the pump may be constructed without alignment pins 48 and 50. In the preferred embodiment shown in FIG. 2, alignment hole 52 is an essentially circular hole, while alignment hole 54 is an elongated hole. In this embodiment, alignment pin 48 and alignment hole 52 provide the indexing of disposable pump chamber 10, and hole 52 is positioned over alignment pin 48 prior to alignment hole 54 being placed over alignment pin 50.

Another important feature of the present invention is the ability to sense the presence of air bubbles in the IV fluid. Air bubbles present a danger to the patient receiving IV therapy, and an alarm must be provided to indicate the presence of air bubbles in the fluid. As shown in FIG. 2, the present invention includes first and second electrodes 56 and 58, which are positioned on the bottom surface of top cover 18. Terminals 60 and 62 are connected to electrodes 56 and 58. Connected to diaphragm enclosure 22 is common electrode 64. Bolts 66 and 66a fasten common electrode 64 to diaphragm enclosure 22 and provides electrical connection to common electrode 64.

By measuring the capacitance between first electrode 56 and common electrode 64 and also the capacitance between second electrode 58 and common electrode 64, the presence of an air bubble passing through disposable pump 10 can be sensed. Electronic circuitry (not shown) is connected to terminals 60, 62 and 66 to detect the difference in dielectric constant between electrodes 56 and 58 and common electrode 64 on the opposite side of disposable pump chamber 10. When an air bubble passes between first electrode 56 and common electrode 64, the electronic circuitry becomes unbalanced, thereby causing an alarm to sound.

In the preferred embodiments of the present invention, top cover 18 is a clear, optical grade, plastic material such as a Plexiglas or similar acrylic plastic. Because top cover 18 is clear, the medical personnel are able to view the fluid as it is passing through the pump to determine whether any air bubbles are present. This is important during the initial setup and purging of the system, since the medical personnel must make sure that all air is out of the system prior to connecting the IV equipment to the patient. The present invention permits the medical personnel to view the fluid as it is pumped during the initial setup stage.

Positioned below latch post 21 is switch 68, as best illustrated in FIG. 2. When top cover 18 is closed, the latch 19 is in closed position (as shown in FIG. D) arm 70 of switch 68 engages the inner surface of latch 19 thereby closing switch 68. Electrical circuitry (not shown) senses whether switch 68 is closed and thereby determines whether the pump is ready to operate. Only when switch 68 is closed will the pump be allowed to operate. This prevents actuation of the pump when cover 18 is not securely closed, and diaphragm enclosure 22 is held in its operating position proximate cam housing 23.

Leaf spring 72 is used to apply a small pressure to the channel 74 of diaphragm 10 so that if a negative pressure exists at the output of the diaphragm, channels 24, 26 and 28 will not collapse. The pressure is just enough to overcome the compliance of the channel of the diaphragm. The negative pressure ensures that the channel is closed. Therefore, only a small amount of pressure is required to overcome the force of the leaf spring 72.

The operation of the IV pump of the present invention is generally as follows. Pistons 38 and 40 are driven so that when piston 38 is moving downward, piston 40 is moving upward. Similarly, when piston 38 is moving upward, piston 40 is moving downward. At the same time, valves 44 and 46 are driven so that at least one of the two valves is closed at all times. When piston 38 is moving downward, valve 44 is down, while valve 46 is up. Conversely, when piston 38 is moving up, valve 44 is in its uppermost position and valve 46 is in its lowermost position.

For the purpose of illustration, it will be assumed that a typical pumping cycle starts when piston 38 and valve 44 are in their uppermost position, and piston 40 and valve 46 are in their lowermost position. First, valve 46 closes. Second, valve 44 moves downward to open. Piston 38 then begins moving downward, thereby increasing the volume of first flexible rolling diaphragm pumping chamber 24. The downward movement of piston 38 draws fluid from the reservoir, through inlet tubing 14 past open valve 44 and into first chamber 24.

At the same time that the first chamber 24 is filling, piston 40 is moving upward, thereby reducing the volume of second chamber 26 and pumping fluid from second chamber 26 through outlet tubing 16, to the patient.

When piston 38 reaches its lowermost position and piston 40 is approaching its uppermost position, valve 44 is driven upward to close fluid flow from the reservoir to first chamber 24. Second valve 46 is then moved downward to permit fluid flow from first chamber 24 to second chamber 26. After the two valves have been moved, piston 38 begins to move upward, thereby reducing the volume of first chamber 24, while second piston 40 moves downward, thereby increasing the volume of second chamber 26. In the preferred embodiment, the rate of decrease of the volume of first chamber 24 is greater than the rate of increase of second chamber 26. As a result, some of the fluid being pumped from first chamber 24 is pumped out through outlet tubing 16 to the patient. In the preferred embodiments, the cross-sectional areas of chambers 24 and 26 and the rate of travel of pistons 38 and 40 are selected so that the amount of fluid being pumped out through outlet tubing 16 is essentially the same when the fluid is being pumped from first chamber 24 as it is when the fluid is being pumped from second chamber 26. As a result, an essentially pulse-free fluid flow is produced with only two pumping chambers and only two valves.

When piston 38 reaches its uppermost position and piston 40 reaches its lowermost position, the pumping cycle is complete, and the next cycle is ready to begin.

During the pumping operation, the volume of pressure sensing chamber 28 depends upon the back pressure from outlet tubing 16 and the patient. Piston 42, which contacts the bottom portion of third flexible diaphragm chamber 28, moves upward and downward as a function of fluid pressure within third chamber 28. Electrical contacts are connected to piston 42, and the state of the contacts (either open or closed) provides an indication of whether the back pressure has exceeded one or more predetermined threshholds. As each threshhold is exceeded, an alarm is produced.

Throughout the operation of the pump, the dielectric constant between electrodes 56 and 58 and common electrode 64 is sensed. If an air bubble passes through disposable pump chamber 10, it is sensed electrically by the difference in dielectric constant between electrodes 56 and 64 and between electrodes 58 and 64.

The Disposable Pump Chamber

Figure 3A:
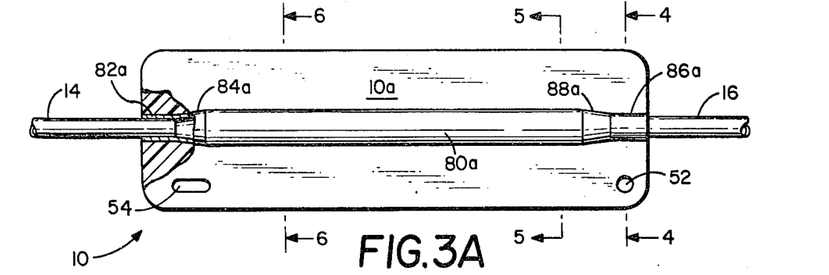
FIGS. 3A, 3B, and 3C are top, side, and bottom views of a preferred embodiment of the disposable pump chamber.
Figure 3B:
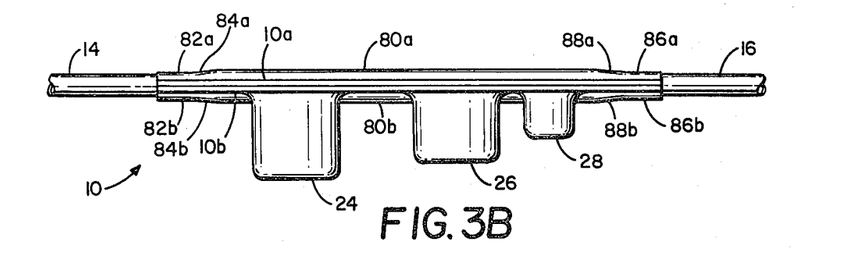
Figure 3C:
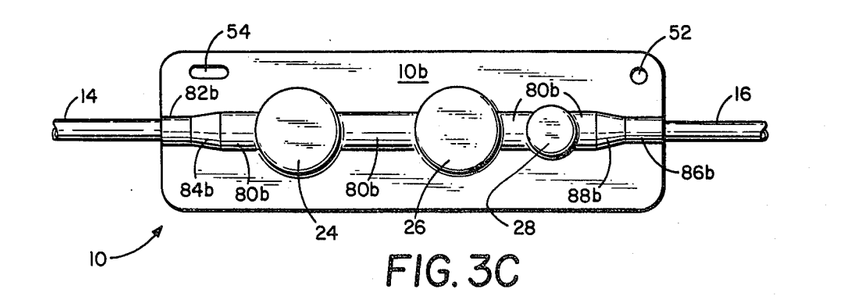
Figure 4:
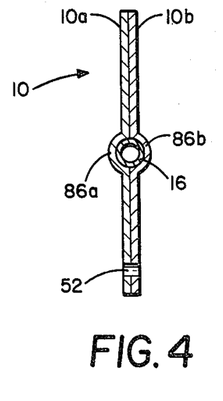
FIG. 4 is a sectional view of the disposable pump chamber along section 4—4 of FIG. 3A.
Figure 5:
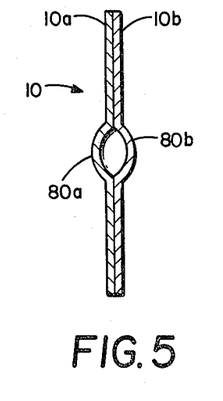
FIG. 5 is a sectional view of the disposable pump chamber along section 5—5 of FIG. 3A.
Figure 6:
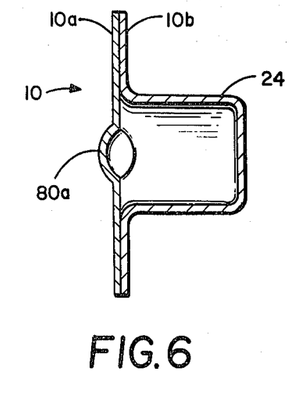
FIG. 6 is a sectional view of the disposable pump chamber along section 6—6 of FIG. 3A.

FIGS. 3A, 3B, 3C and 4–6 show disposable pump chamber 10 in greater detail. FIGS. 3A, 3B and 3C are top, side and bottom views, respectively. FIGS. 4, 5 and 6 are sectional views at different positions of disposable pump chamber 10.

In the preferred embodiments of the present invention, disposable pump chamber 10 is made of two parts, upper part 10a, and lower part 10b, which are preferably made out of flexible plastic material which is capable of heat sealing. In one preferred embodiment, both upper part 10a, and lower part 10b are formed of a vinyl plastic material.

Both upper part 10a and lower part 10b are vacuum formed or blow molded to define the passages and chambers of disposable pump chamber 10. Upper part 10a is primarily a planar sheet, except for a raised portion 80a which extends substantially the entire length of upper part 10a. Raised portion 80a is the top half of a main flow passage which carries fluid from inlet tubing 14 at one end of disposable chamber 10 to outlet tubing 16 at the opposite end. The radii of inlet tubing 14 and outlet tubing 16 are smaller than the radius of portion 80a. At the inlet end of part 10a is an inlet section 82a which has an inner radius which is substantially the same as the outer radius of inlet tubing 14. Connecting inlet section 82a with main flow passage 80a is tapered section 84a, which provides a gently tapered transition from inlet section 82a to main flow passage 80a. At the opposite end of top part 10a is an outlet section 86a and a tapered section 88a. Outlet section 86a has an inner radius which is approximately equal to the outer radius of outlet tubing 16. Tapered transition 88a provides a gentle transition from main flow passage 80a to outlet section 86a.

Lower part 10b of disposable pump chamber 10 has a similar main flow passage 80b, inlet section 82b, tapered transition section 84b, outlet section 86b and tapered transition 88b. Also formed in lower part 10b and extending downward are first and second flexible rolling diaphragm pumping chambers 24 and 26, and flexible rolling diaphragm pressure sensing chamber 28.

Upper part 10a must be flexible enough to allow closing by leaf spring 72. Lower part 10b must be sufficiently flexible to permit rolling diaphragm action of chambers 24, 26 and 28. In addition, it must be sufficiently flexible to permit valve 44 (shown in FIG. 2) to collapse the section of main flow passage 80b between tapered transition section 84b and first pumping chamber 24 and to permit the valve 46 to similarly collapse the section of main flow passage 80b between first and second pumping chambers 24 and 26.

As stated previously, top and bottom parts 10a and 10b are preferably a plastic material which is easily sealed by heat sealing. Parts 10a and 10b are heat sealed together at the time of forming or in a subsequent operation. The mating surfaces of 10a and 10b may be of a lower melting point material therefore aiding the sealing process. Inlet tubing 14 and outlet tubing 16 are also preferably clear material which is heat sealed with the top and bottom parts 10a and 10b.

Although heat sealing is one preferred means of sealing the top and bottom parts 10a and 10b together with tubing 14 and 16, sealing can also be accomplished by ultrasonic welding, rf sealing, solvent bonding, or other sealing techniques.

In one preferred embodiment, disposable pump chamber 10 is formed by blow molding. In this case, upper part 10a and lowert part 10b are heat sealed together with tubings 14 and 16 at the time of the molding operation. The advantage of blow molding is that it avoids any registration problems which may otherwise be encountered in attempting to attach together separately molded top and bottom parts 10a and 10b.

Alternately, vacuum molding of the individual top and bottom parts 10a and 10b may be used. In this embodiment, multiple cavity molds are used to produce molded plastic sheets containing many of the same parts (either 10a or 10b). Tubins 14 and 16 are then placed into position, and a sheet having an identical number of the other part is then placed into position over the first sheet and the tubing, and parts 10a and 10b are heat sealed together. The individual pump chambers are then severed from one another by a punch and die type cutter. At the same time, the registration holes 52 and 54 are punched out to their exact desired size. In this manner, large number of disposable pump chambers 10 can be fabricated at the same time.

The Pump Housing

Figure 7:
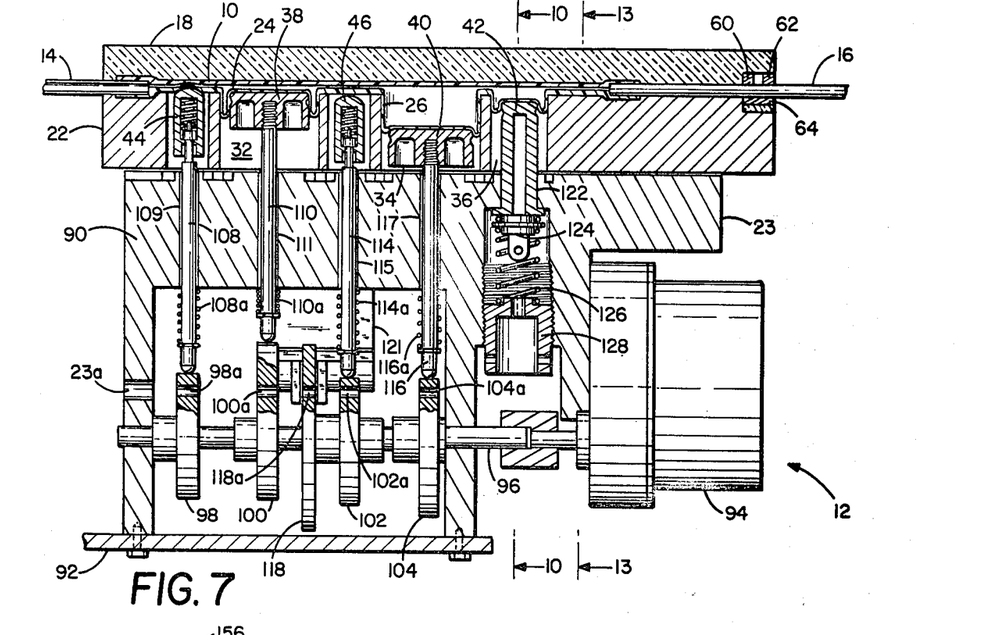
FIG. 7 shows a sectional view of the IV pump along section 7—7 of FIG. 1.

FIGS. 7-13 show various portions and views of pump housing 12. FIG. 7 is a sectional view which shows pump housing 12 in operation with top cover 18 closed and disposable pump chamber 10 inserted. The pump is shown at the beginning of a pumping cycle.

As shown in FIG. 7, diaphragm enclosure 22 is mounted on top of cam housing 23, which in a preferred embodiment is a low friction structural material such as Delrin, or a material such as ABS with linear bearings used to reduce friction of valve and piston rods. Cam housing 23 is connected to mounting plate 92 at its base.

Supported on cam housing 23 is motor 94, which is preferably a stepper motor. Although other drive motors can be used, a stepper motor is particularly advantageous due to its digital nature, which is well suited for control by digital circuitry, such as a microcomputer control circuit.

Motor 94 drives cam shaft 96. Attached to cam shaft 96 are four cams 98, 100, 102 and 104. Cam 98 drives valve 44 through rod 108, which has its lower end rounded to ride on cam 98 and which extends through shaft 109 in cam housing 90. Valve 44 is spring loaded to facilitate loading of pumping chamber 10 into pump housing 12.

Cam 100 drives piston 38 through rod 110, which extends through shaft 111 in cam housing 90. The bottom end of rod 110 rides on cam 100, while the upper end is threaded to permit attachment of piston 38. The threaded connection of rod 110 and piston 38 permits adjustment of the effective length from cam 100 to the top of piston 38, thereby reducing the requirement for close tolerances.

Valve 46 is driven by cam 102 through rod 114, which has a rounded lower end riding on cam 102 and which passes through shaft 115 in cam housing 90. Valve 46 is also spring loaded to facilitate loading of pumping chamber 10 into the pump housing 12.

Cam 104 drives piston 40 by means of rod 116, which extends through shaft 117 in cam housing 90. The lower end of rod 116 is rounded to ride upon the surface of cam 104, and the upper end of rod 116 is threaded for connection to piston 40.

Each of the four rods 108, 110, 114, and 116 has a small spring, 108a, 110a, 114, and 116a near the bottom end of the respective rod. These springs are preferably very weak springs, and are used solely to assure that the rods follow their respective cams at all times. This is particularly important when the pump is operating in a vertical rather than a horizontal orientation (i.e. rods 108, 110, 114, and 116 are generally horizontal). Springs 108a, 110a, 114a, and 116a are made as weak as possible so that very little energy is expended in driving the pistons and valves against the spring force.

The drive system for pistons 38 and 40 and valves 44 and 46 has signficant advantages. Motor 94 drives shaft 96 in only one direction; no reversal of motion of drive motor 94 is required in order to provide the desired pumping action. In addition, because chambers 24 and 26 of disposable pump chamber 10 are rolling diaphragm type chambers, tolerances for cylinders 32 and 34, and the cam riders and rods are significantly reduced. This permits lower manufacturing costs, while still providing the necessary accuracy in pumping rates.

Also connected to drive shaft 96 in FIG. 7 is an encoder wheel 118, which is a conventional encoder wheel having slots near its periphery at predetermined spacing. A conventional encoder sensor assembly 120 is mounted to the back surface of cam housing 90 and is positioned to sense the slots in encoder wheel 118. Encoder sensor assembly 120 typically includes a light source (not shown) positioned at one side of encoder wheel 118 and a light sensor (not shown) positioned at the opposite side. Each time a slot in wheel 118 is encountered, a light is permitted to pass from the light source to the light sensor, and encoder sensor assembly 120 produces an electric pulse indicating the presence of a slot in encoder wheel 118.

Figure 8:
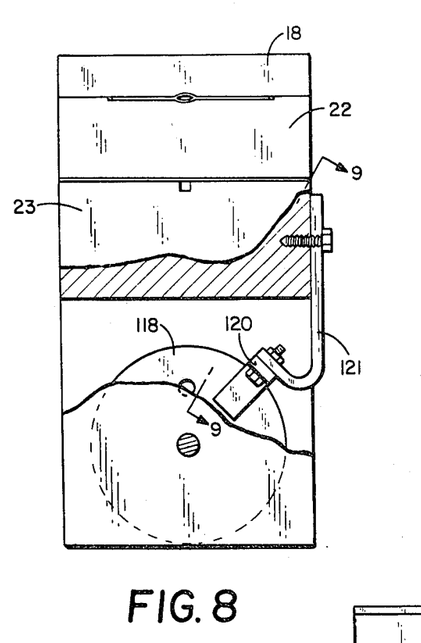
FIGS. 8 and 9 are detail views showing the encoder apparatus of the IV pump.
Figure 9:
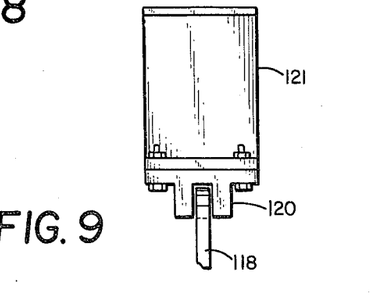

FIGS. 8 and 9 show the encoder assembly 120 in greater detail. As shown in FIGS. 8 and 9, encoder assembly 120 is attached to a flange 121, which in turn is connected by screws to the back surface of cam housing 23.

The purpose of encoder wheel 118 and encoder sensor assembly 120 is to provide a direct indication that cam shaft 96 is rotating. In a preferred embodiment of the present invention, control circuitry (not shown) monitors the output of encoder sensor 120. If a change in the output of encoder sensor 120 does not occur within a predetermined time interval, an alarm is produced and pumping is terminated. This sensing provides direct indication of whether shaft 96 is turning and, therefore, the pump is pumping. It is possible that motor 94 may be receiving drive signals from the control circuitry and yet, due to some malfunction, shaft 96 is not turning. The use of encoder wheel 118 and encoder sensor assembly 120 provides an indication of this failure mode.

As shown in FIG. 7, each of the cams 98, 100, 102, and 104 has an alignment hole 98a, 100a, 102a, and 104a, respectively. Similarly, encoder wheel 118 has an alignment hole 118a. Cam housing 23 also includes an alignment hole 23a which is used in conjunction with alignment holes 98a, 100a, 102, 104, and 118a to set the initial alignment of each of the cams. By placing a pin (not shown) through hole 23a and then through each of succeeding holes, all of the cams may be lined up during initial assembly of the pump. The cams and encoder wheel may then be locked into place on cam shaft 96 by set screws (not shown). Alignment may also be accomplished by sloting shaft 96 and keying the cams and encoder wheel.

FIG. 7 also illustrates the back pressure sensor assembly, which includes cylinder 36 and piston 42, together with pressure sensing rolling diaphragm chamber 28 of disposable pump chamber 10. As shown in FIG. 7, piston 42 extends through shaft 122 in cam housing 90. Connected to the bottom of piston 42 is terminal 124, which receives the top end of spring 126. The opposite end of spring 126 engages the top surface of threaded member 128. It can be seen, therefore, that the fluid pressure within pressure sensing chamber 28 acts on piston 42 in a generally downward direction, while spring 126 provides an upward force.

Figure 10:
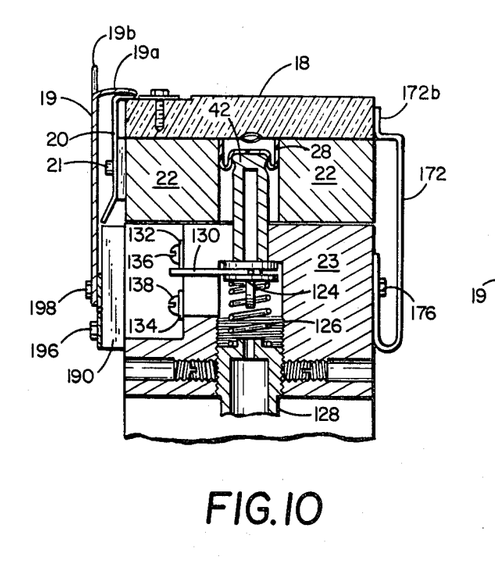
FIG. 10 is a sectional view of the IV pump along section 10—10 of FIG. 7.

Extending from terminal 124 is contact arm 130, which is best shown in FIG. 10. First and second pressure limit contacts 132 and 134 are positioned at two different vertical positions at the front surface of cam housing 90. In its normal position, spring 126 applies sufficient force to piston 42 so that contact arm 130 is in physical and electrical contact with the bottom edge of upper contact 132. Electrical connection to contact arm 130 is made through a wire (not shown) connected to terminal 124, and electrical connection to contact 132 is made by a wire (not shown) connected between one of the screws 136 and contact 132.

As long as pressure within chamber 28 is insufficient to overcome the spring force of spring 126 and separate contact arm 130 and contact 132, the back pressure is within acceptable limits. Since fluid from back pressure sensing chamber 28 goes directly to tube 16, which in turn connects to the IV needle, the pressure at chamber 28 is directly related to the forcing pressure at the patient. If the preset pressure (which is determined by spring 126, the position of threaded member 128, and the position of contact 132) is exceeded so that piston 42 moves downward and contact arm 130 and contact 132 are separated, the break in the electrical contact is sensed and an alarm is produced.

In the preferred embodiment of the present invention, a second lower contact 134 is positioned below upper contact 132. When a second, higher pressure is reached, contact arm 130 engages the top edge of lower contact 134. This is also electrically sensed, and is used to provide a second alarm indicative of a second, higher back pressure. Screws 138 hold lower contact 134 in place. An electrical wire (not shown) is connected between one of the screws 138 and lower contact 134. The electric control circuit (not shown) allows the operator to select which pressure limit activates an alarm (low or high).

Figures 11, 12:
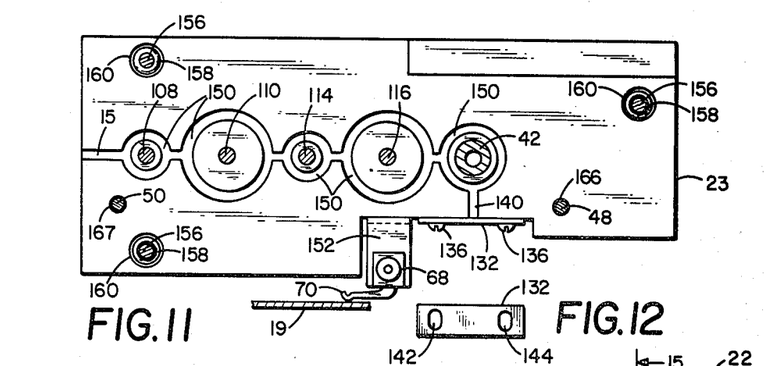
FIG. 11 is a top view of the cam housing of the IV pump.
FIG. 12 is a detail view showing a back pressure contact.

FIG. 11 is a top view of cam housing 23, and FIG. 12 is a detailed view of contact 132. These two figures further illustrate the back pressure sensing mechanism of the present invention. As shown in FIG. 11, cam housing 23 has a narrow slot 140 within which contact arm 130 moves.

FIG. 12 shows a front view of contact 132, which is a rectangular metallic plate having two slotted openings 142 and 144. Slotted holes 142 and 144 permit vertical adjustment of plate 132, which permits adjustment of the pressure at which the contact between plate 132 and contact arm 130 is broken. Lower contact 134 has similar slotted holes to permit an adjustment of the position of lower contact 134 in a similar manner.

The back pressure sensing mechanism of the present invention is very inexpensive, simple, and reliable. It permits adjustment of two pressure limits at which alarms are produced. Because the present invention permits selection of back pressure limits at which alarms will sound, the patient, in case of an infiltration, is not subjected to the maximum back pressure that the pump is able to supply. This has been a continuing problem with prior art IV pumps, since the maximum back pressure of the pump is often beyond the safe limit for a particular patient or application.

Although a piston, spring, contact arm and contacts are used in the preferred embodiment shown in the Figures, other means of sensing the movement of chamber 28 due to back pressure may also be used. For example, solid state or wire strain gauges may be used to sense pressure as a result of displacement of piston 42. The embodiment shown in the Figures however, is particularly advantageous due to its low cost, simplicity, reliability and easy adjustment.

FIG. 11, which is a top view of cam housing 90, also shows grooves 150 which surround each opening in cam housing 23. These grooves catch any liquid which might be spilled in the event of a leak in disposable pump chamber 10 and prevent fluid from flowing into the bearing surfaces between each rod and their respective shafts in housing 23.

Figure 13:
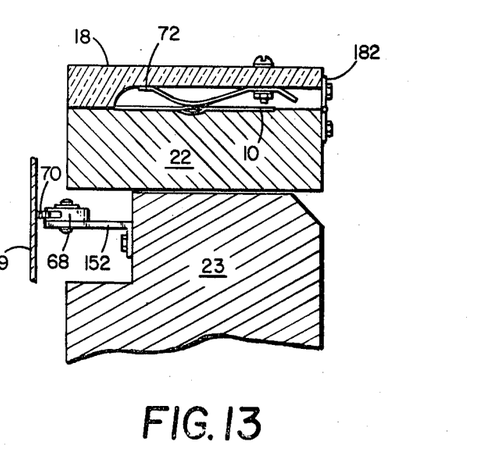
FIG. 13 is a sectional view along section 13—13 of FIG. 7.

FIGS. 11 and 13 show switch 68 and switch arm 70 in further detail. Switch arm 70 engages the inner surface of latch 19 when the entire pump assembly is latched together. This causes switch 68 to be closed, which in turn indicates that the pump is ready for operation. Switch 68 is mounted on mounting flange 152, which is in turn connected to cam housing 23.

Figure 14:
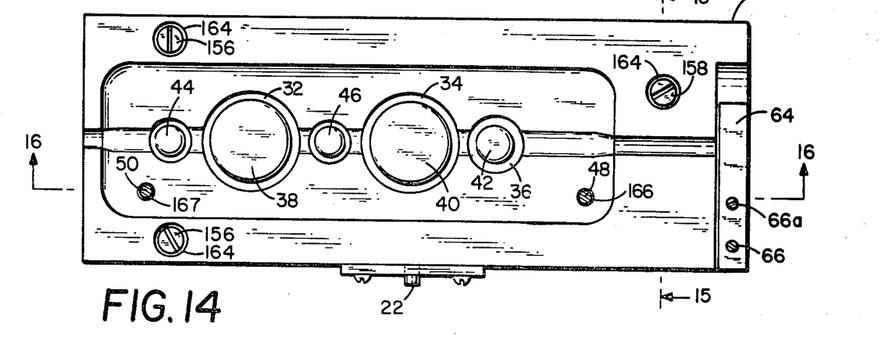
FIG. 14 is a top view of the diaphragm enclosure of the IV pump.

FIG. 14 is a top view of diaphragm enclosure 22. FIG. 14, together with FIG. 2, illustrates the bubble sensor which is used to detect the presence of air bubbles in disposable pump chamber 10. The bubble sensor includes first and second electrodes 56 and 58, which are located on the bottom surface of top cover 18. Terminals 60 and 62 make electrical contact with first and second electrodes 56 and 58, respectively.

Common electrode 64 is attached to the top surface of the diaphragm enclosure 22 and is held in place by terminal screws 66 and 66a. The width of common electrode 64 is greater than the width of either first electrode 56 or second electrode 58, and common electrode 64 is positioned so that it is directly opposite both first electrode 56 and second electrode 58. Tube 16 fits between first and second strips 56 and 58 and common electrode 64. Electronic circuitry (not shown) connected to terminals 60, 62, and 66 detects the difference in dielectric constant between the first capacitor defined by first electrode 56 and common electrode 64 and the second capacitor defined by second electrode 58 and common electrode 64. When an air bubble reaches the first capacitor, the electronic circuitry becomes unbalanced, thereby indicating the presence of an air bubble. This unbalance is used to trigger an alarm.

The bubble detector shown in the Figures is simple, easily incorporated into the pump, and inexpensive. It does not require optical techniques in order to sense air bubbles, as have been used in prior art IV pumps. As a result, problems encountered with optical techniques are avoided.

The presence of air in an IV system must be avoided. The pump of the present invention is designed to avoid any chance of air bubbles accumulating within disposable pump chamber 10. Each of the rolling diaphragm chambers 24, 26, and 28 is oriented so that air bubbles can escape upwards at all times, and will not accumulate within the chambers. Similarly, valves 44 and 46 operate in a manner which does not lead to creation of air bubbles within disposable chamber 10.

In a preferred embodiment of the present invention, the entire pump mechanism is oriented so that the inlet end is lower than the outlet end. As a result, there is a natural tendency for any air bubbles to flow through the pump, rather than accumulate at any point within disposable chamber 10. This is particularly important during the initial purging of the system, since all air must be removed from chamber 10 before connection is made to the patient.

Figure 15:
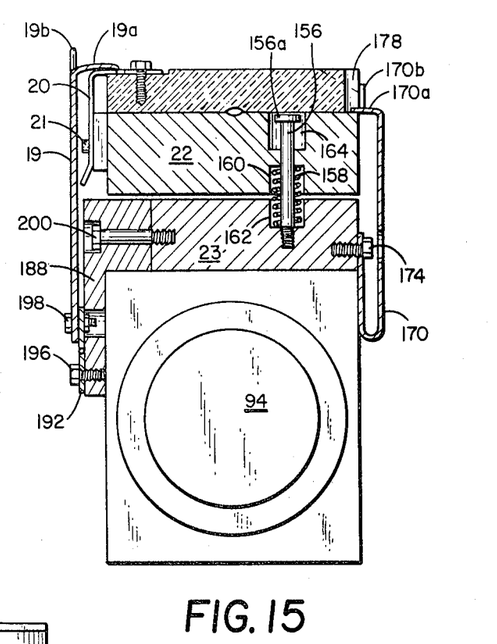
FIG. 15 is a sectional view along section 15—15 of FIG. 14.

FIGS. 14 and 15 illustrate how diaphragm enclosure 22 is spring mounted to cam housing 23. In normal operation, the bottom surface of diaphragm enclosure 22 is spaced from the top surface of cam housing 23 by about 0.050 inches. Diaphragm enclosure 22 is held in place with respect to cam housing 23 by three screws 156, which extend downward through diaphragm enclosure 22 and are threaded into cam housing 23. As best illustrated in FIG. 15, a spring 158 surrounds the shaft of each of screw 156 and is mounted in recesses 160 and 162 of diaphragm enclosure 22 and cam housing 23, respectively. When the pump is normal operation, spring 158 is compressed and urges the surfaces of cam housing 23 and diaphragm enclosure 22 slightly apart.

When latch 19 is released and pivoted downward and latch 20 is pulled upward away from latch pin 21, spring 158 urges diaphragm enclosure 22 away from cam housing 23 until the top end 156a of screw 156 engages the bottom of recess 164 in diaphragm enclosure 22.

Figure 16:
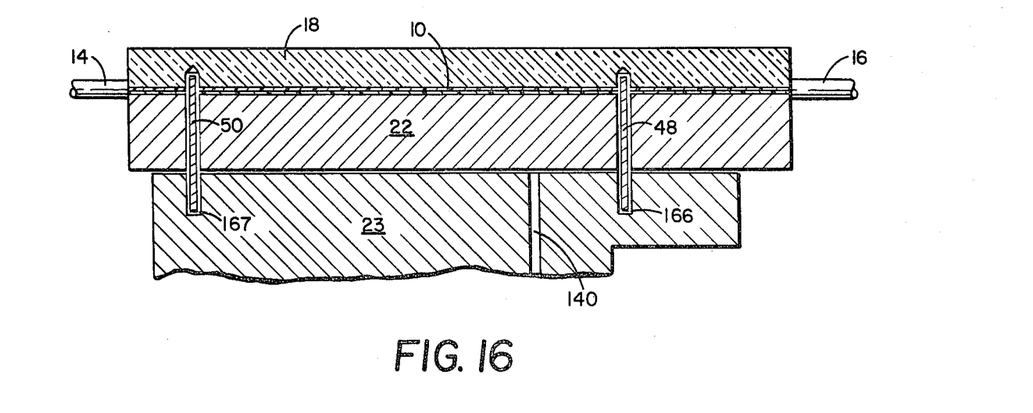
FIG. 16 is a sectional view along section 16—16 of FIG. 14.

Proper orientation of diaphragm enclosure 22 with respect to cam housing 23, as well as registration of disposable pump chamber 10 with respect to both diaphragm enclosure 22 and cam housing 23, is provided by registration pins 48 and 50. As shown in FIG. 16, pins 48 and 50 extend from the top surface of diaphragm enclosure 22 downward through diaphragm enclosure 22 into shafts 166 and 167, respectively, in cam housing 23.

As described previously, diaphragm enclosure 22 is spring mounted with respect to cam housing 23 so that during the removal and insertion of disposable pump chamber 10 all pistons and valves are in a recessed position with respect to the top surface of diaphragm enclosure 22. This ensures that disposable pump chamber 10 can be placed in position without any interference from the valves or pistons, regardless of where in the cycle the pump has stopped. As shown in the preceding Figures, top cover 18 is latched closed with respect to diaphragm enclosure 22 by latch 20 and latch post 21.

Top cover 18 and diaphragm enclosure 22 are in turn held in position with respect to cam housing 23 by latch 19, which is attached by a hinge connection at one end to cam housing 23. Latch 19 has a flap portion 19a and a grasping handle portion 19b. Flap 19a hooks over the top surface of latch 20 and holds the various positions of the pump in their desired operating position.

Figure 17:
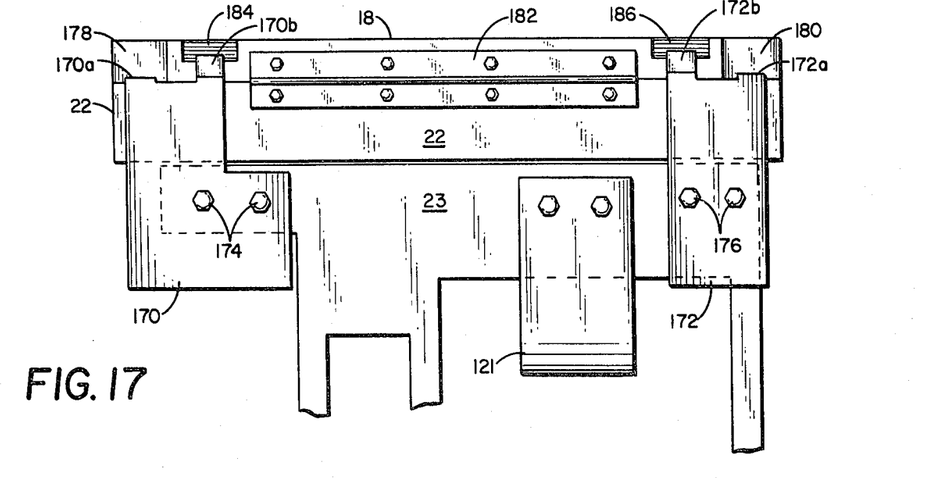
FIG. 17 is a rear view of the IV pump.
Figure 18:
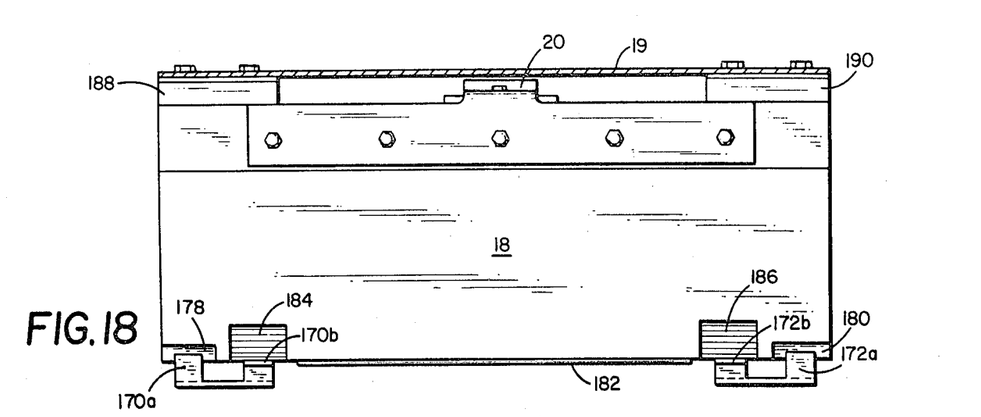
FIG. 18 is a top view of the IV pump.
Figure 19:
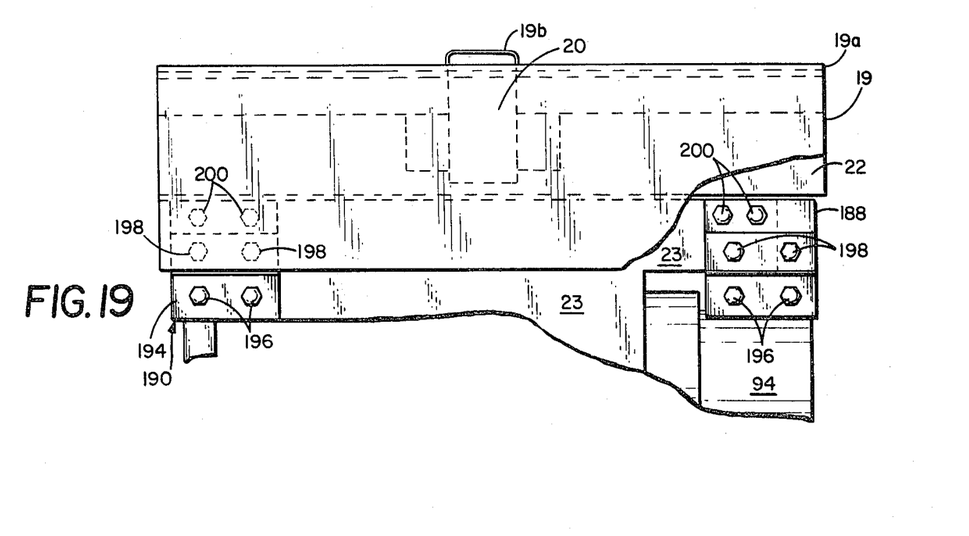
FIG. 19 is a front view of the IV pump, with a portion of the latch broken away.

When latch 19 is pivoted downward or away from top cover 18, top cover 18 and diaphragm enclosure 22 do not immediately spring upward. Rather, they only move away from cam housing 23 after top cover 18 is partially open. FIGS. 17, 18 and 19 further illustrate the unique latch and hinge mechanism of the pump. FIG. 17 is a rear view of pump housing 12; FIG. 18 is a top view; and FIG. 19 is a front view. As shown in FIGS. 17 and 18, and as also partially illustrated in FIGS. 10 and 15, attached to the back surface of cam housing 23 are metal members 170 and 172, which act as a leaf spring type latching and camming mechanism at the back of top cover 18. Member 170 has a latching portion 170a and a camming portion 170b. Similarly, metal member 172 has a latching portion 172a and a camming portion 172b. Member 170 is connected to the back surface of cam housing 23 by screws 174, while member 172 is attached to back surface of cam housing 23 by screws 176.

When the pump is closed and in operation, the forward ends of latching portions 170a and 172a engage the bottom surfaces of recesses 178 and 180 at opposite ends of the back of top cover 18. Latch members 170a and 172a, together with latch 19, prevent spring 158 from separating the diaphragm enclosure 22 and cam housing 23 more than the desired 0.050 inches.

As shown in FIG. 17, top cover 18 and diaphragm enclosure 22 are pivotally connected to one another along their back surfaces by hinge 182. When cover 18 begins to open, it pivots about an axis defined by hinge 182. Camming portions 170b and 172b act against the back surface of cover 18 to push the upper end of metal members 170 and 172 away from the back surfaces of cover 18 and diaphragm enclosure 22. When cover 18 has been opened a sufficient amount, the camming action caused by portions 170b and 172b finally moves latching portions 170a and 172a out of engagement with recessed portions 178 and 180 of top cover 18. Since latch 19 has already been pivoted to an open position, the movement of portions 170a and 172a out of engagement with recesses 178 and 180 permit diaphragm enclosure 22 and top ccover 18 to be moved upwardy by the force of springs 158.

Once diaphragm enclosure 22 and cam housing 23 have been separated, cover 18 may be opened further to permit removal and replacement of disposable pumping chamber 10. Sloped ramp portions 184 and 186 permit top cover 18 to be further opened without interference with camming portions 170b and 172b of metal members 170 and 172.

As illustrated in FIGS. 15, 18 and 19, latch 19 is connected to cam housing 23 by front attachment blocks 188 and 190. The lower portions of hinges 192 and 194 are connected by screws 196 to the lower ends of front attachment blocks 188 and 190, respectively. The upper portions of hinges 192 and 194 are attached by bolts 198 to the bottom end of latch 19. Screws 200 connect front attachment blocks 188 and 190 to the front surface of cam housing 23.

Figure 20:
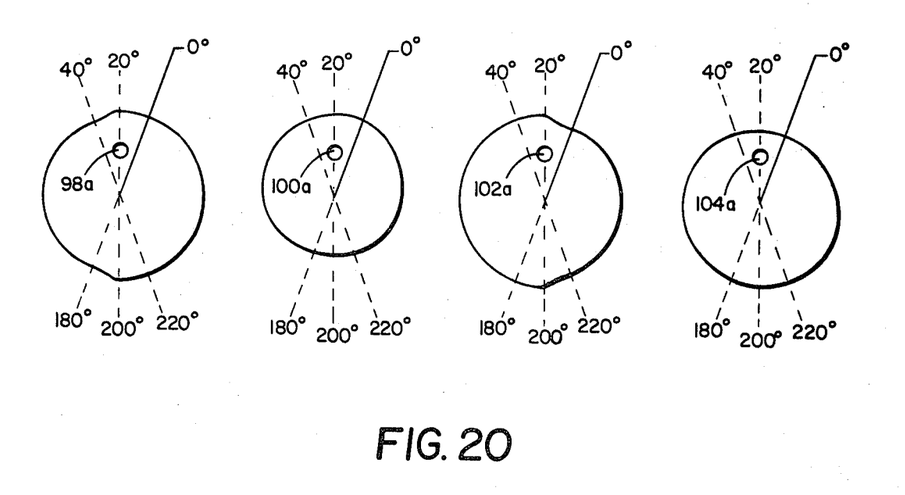
FIG. 20 shows the four cams used to drive the first and second valves and the first and second pistons of the pump.

FIG. 20 shows a preferred embodiment of cams 98, 100, 102, and 104. Each cam is shown as viewed from the direction of motor 94. In the embodiment shown in FIG. 13, cams 98, 100, 102, and 104 rotate in a clockwise direction.

At the zero degree (0°) reference point (i.e. the beginning of a pumping cycle), valve 44 is closed because cam 98 is at a maximum radius. Cam 100 is at the start of a constant maximum radius; therefore, piston 38 is stationary at the maximum vertical position. Cam 102 is at a minimum radius so that valve 46 is open. Cam 104 is increasing in radius at a rate of 0.666 mils per degree rotation so that piston 40 is moving upward at a rate of 0.666 mils per degree rotation. At this stage of operation, the volume of fluid that is being pumped per degree rotation is equal to 0.666 mils times the cross-sectional area of second pumping chamber 26 (and second cylinder 34), plus 0.666 mils times one-half the cross-sectional area between the inner walls of the pump chamber and the piston.

At a rotation of 20°, valve 44 is still closed, piston 38 is still stationary, valve 46 is now closed because cam 102 is at the maximum radius. Piston 40 continues to move upward at a rate of 0.666 mils per degree rotation.

At a rotation of 40°, valve 44 has opened because cam 98 is at its minimum radius. At this point, piston 38 is still stationary, the valve is still closed, and cam 104 is moving piston 40 up at the rate of 0.666 mils per degree rotation.

At a rotation from 40° to 180°, valve 44 is open, the radius of cam 100 is decreasing at the rate of 1.714 mils per degree rotation. As a result, first pumping chamber 24 is filling at a rate of 1.714 mils times the cross-sectional area of first chamber 24 per degree rotation plus 1.714 mils times one-half the cross-sectional area between the inner walls of the pump chamber and the piston. Valve 46 is still closed, and piston 40 continues to move up at a rate of 0.666 mils per degree rotation.

At 180° rotation, valve 44 is still open and cam 100 begins a 40° section (i.e. from 180° to 220°) in which it is at a constant minimum radius. Piston 38, therefore, is at its lowermost position and is stationary. Valve 46 is still closed, while cam 104 is still increasing in radius at a rate of 0.666 mils per degree rotation.

At 200° rotation, cam 98 has increased to its maximum radius and, therefore, valve 44 is in its uppermost position and has closed fluid flow from inlet tubing 14. Cam 100 is at its constant minimum radius and piston 38 is still stationary at its lowermost position. Valve 46 is still in its uppermost position thereby closing fluid passage from first chamber 24 to second chamber 26. The radius of cam 104 continues to increase at a rate of 0.666 mils per degree rotation and piston 40 continues to move upward at that rate.

At 220° rotation, valve 44 remains in its upward closed position and piston 38 remains in its stationary lowest position. Cam 102 has now reached its minimum radius so that valve 46 is in its lowermost position and is open. Cam 104 reaches its maximum radius at the 220° rotation position.

From 220° to 360° rotation, valve 44 is at its uppermost (closed) position. Cam 100 is increasing in radius at a rate of 1.714 mils per degree rotation and, therefore, piston 38 is moved upward at this rate. Valve 46 is in its lowermost (open) position, thereby permitting fluid flow from first chamber 24 to second chamber 26. Cam 104 is decreasing in radius at a rate of 1.048 mils per degree rotation, and therefore, piston 40 is moving down at this rate. The volume of fluid pumped out through outlet tubing 16 per degree rotation is equal to the difference in volume change between first chamber 24 and second chamber 26. In the preferred embodiment, first and second chambers 24 and 26 have identical cross-sectional area, and the difference in volume is merely the difference between 1.714 mils per degree rotation decrease in volume of first chamber 24 and 1.048 mils per degree of rotation increase in volume of second chamber 26. The volume of fluid pumped is, therefore, the difference between 1.714 mils minus 1.048 mils per degree of rotation times the cross-sectional area of either cylinder 38 or 40 plus the difference between 1.714 mils minus 1.048 mils per degree rotation times one-half the cross-sectional area between the inner walls of the pump chamber and the piston. This corresponds to 0.666 mils per degree rotation times the cross-sectional area of second cylinder 26 plus 0.666 mils times one-half the cross-sectional area between the inner walls of the pump chamber and the piston. As a result, the volume being pumped remains constant even when second piston 40 is moving downward. This is because the volume being pumped out of first chamber 24 exceeds the volume being received in second chamber 26 by an amount equal to the desired constant volume flow rate.

When cams 98, 100, 102, and 104 reach the 360° (or 0°) rotation, the next cycle begins. It can be seen, therefore, that a constant flow rate output is provided with only two valves and two cylinders. No reversal of drive direction is required from motor 94 in order to provide the pumping action.

In the specific example described, the cross-sectional areas of first and second chambers 24 and 26 are equal. This provides some advantages in fabrication, particularly since both first piston 38 and second piston 40 are of the same size and may be interchangeable. It is possible, however, to use chambers of different cross-sectional area. The particular drive rates of first and second pistons 38 and 40 depend, of course, on the cross-sectional areas of first and second chambers 24 and 26 so that the fluid flow rate at outlet tubing 16 remains constant regardless of the direction of movement of the pistons.

With the pump of the present invention, the volume of fluid delivered is dependent almost entirely on the dimensions of cams 100 and 104 and pistons 38 and 40. The volume of fluid delivered depends only very slightly on the thickness of first and second pumping chambers 24 and 26. For most applications, the effect of wall thickness of chambers 24 and 26 can be considered to be negligible.

It can also be seen that the point at which valves 44 and 46 change positions is not critical as long as one closes before the other opens, and that all valve changes take place during a constant radius portion of cam 100.

A significant advantage of the present invention is all valve and piston movements are timed off of a single cam shaft 96. The valves operate in a continuous manner according to the shape of cams 98 and 102, without electronic sensing or spring actuation.

The pump of the present invention also provides fail safe operation. As illustrated in FIG. 20, at least one valve is closed throughout the entire pumping cycle. There is no danger of siphoning in the event that the pump is stopped due to power failure, inadvertent shutdown, or any other cause.

Conclusion

The pump of the present invention has significant advantages over the prior art IV pumps. First, the IV pump of the present invention is small, accurate, reliable, and economical to manufacture and use.

Second, disposable chamber 10 is an extremely low cost component. As will be discussed in detail later, disposable chamber 10 is preferably fabricated out of plastic. Since there are no internal valves in disposable chamber 10, the cost of disposable chamber 10 is low.

Third, disposable pump chamber 10 has no seals between moving parts, due to the use of rolling diaphragm pumping chambers 24 and 26, and external valves which merely pinch off fluid flow within the disposable pump chamber 10. Because no seals between moving parts are required, the pump does not cause damage to blood cells and may be used to administer whole blood.

Fourth, the disposable pump chamber provides an effective germ barrier. Chamber 10 is disposable, and is used for only a single IV therapy. Due to the low cost of disposable chamber 10, the cost of intravenous therapy is not limited by the cost of the mechanism.

Fifth, the tolerances of both pump housing 12 and disposable chamber 10 do not appreciably affect the overall accuracy of the pump. As a result, low cost fabrication of disposable chamber 10 is possible.

Sixth, the external valving provided by the valves 44 and 46 does not require critical timing with relationship to the pumping mechanism. The operation of valves 44 and 46 is at a relatively low rate, and is coordinated with the operation of pistons 38 and 40 so that sufficient time is provided for valves 44 and 46 to open and close.

Seventh, the pump provides a substantially continuous flow while using only two valves. The present invention, therefore, provides increased efficiency in pumping with reduced hardware cost.

Eighth, a single drive mechanism drives pistons 38 and 40 and valves 44 and 46. In addition, the drive mechanism does not require reversal of rotation in order to provide the desired movement of the two pistons and two valves. This significantly reduces the complexity of the pump, while increasing the reliability of operation.

Ninth, the pump does not require stretching of an elastomer material, as is required with some peristaltic and pulsating pumps. The possibility of air entering the infusion solution as a result of stretching of an elastomer material, therefore, is eliminated.

Tenth, the pump of the present invention does not pump against an elastomer material, a biasing spring (except to overcome friction), or friction seals. The pump of the present invention, therefore, makes efficient use of energy in providing the pumping action.

Eleventh, the pump of the present invention is automatically biased off in the case of power or battery failure, or being inadvertently shut off, or any other situation in which the pump is stopped. This is because one of the two valves 44 and 46 is always closed, regardless of where the pump is in a pumping cycle. One valve is permitted to open only after the other valve has closed. This provides fail safe operation and prevents any siphoning action if the pump is stopped.

Twelfth, the pump provides a low cost and simple means of sensing and alarming when preset selectable back pressure limits are exceeded. Pressure sensing chamber 28 and piston 42 provide a simple, yet effective method of selecting one or more back pressure limits which trigger alarms. With the pump of the present invention, therefore, back pressure limits can be selected which are less than the maximum back pressure that the pump is able to supply. This provides increased safety for the patient in the case of infiltration or other forms of occlusion.

Thirteenth, the present invention provides a simple, yet effective air bubble detection system. The change in dielectric constant between air and fluid is a low cost, simple, yet effective means of sensing air within the fluid. Alarms are provided to alert medical personnel to the presence of the air within the pump.

Although the present invention has been described with reference to preferred embodiments, workers skilled in the art will recognize that changes may be made in form and detail without departing from the spirit and scope of the invention. For example, although intravenous therapy applications are a particularly important use of the present invention, other pumping requirements can also be met by the pump of the present invention.

What is claimed:

1. A volumetric infusion pump for pumping fluid from a source to a patient comprising:
   a pump inlet for receiving fluid from the source;
   a pump outlet for supplying fluid under pressure to the patient;
   a first pumping chamber having a first cylinder, a first piston, first flexible diaphragm means between the first cylinder and the first piston, a first inlet, and a first outlet, the first pumping chamber having a variable volume depending upon the relative positions of the first cylinder and first piston;
   a second pumping chamber having a second cylinder, a second piston, second flexible diaphragm means between the second cylinder and the second piston, the second inlet connected to the first outlet, and a second outlet, the second pumping chamber having a variable volume depending upon the relative position of the second cylinder and second piston;
   a third chamber having a third inlet and a third outlet, the third inlet being connected to the second outlet and the third outlet being connected to the pump outlet, the third chamber comprising a third cylinder, a third piston, and a third flexible diaphragm means between the third cylinder and the third piston so that the third piston moves in the third cylinder as a function of fluid pressure within the third chamber;
   means for sensing fluid pressure within the third chamber by sensing position of the third piston;
   first valve means for controlling fluid flow between the pump inlet and the first inlet;
   second valve means for controlling fluid flow between the first outlet and the second inlet;
   drive means for causing relative motion of the first cylinder and first piston and relative motion of the second cylinder and second piston;
   valve control means for controlling the first and second valve means such that one of the first and second valve means is closed at all times; and
   wherein the first, second and third flexible diaphragm means, the pump inlet and the pump outlet form an integral disposable unit having a sealed main fluid flow passage between the pump inlet and the pump outlet, so that fluid is pumped from the pump inlet to the pump outlet without physically contacting the housing, the cylinders, the pistons, the valve means, the drive means, or the valve control means.

2. The volumetric infusion pump of claim 1 wherein the means for sensing fluid pressure within the third chamber comprises:
   a movable electric contact connected to and movable with the third piston;
   a first fixed contact located at a fixed position with respect to the third chamber; and
   spring means for applying a spring force to the third piston in a direction opposite to force supplied by fluid pressure within the third chamber.

3. The volumetric infusion pump of claim 2 wherein the movable electric contact breaks contact with the first fixed contact when a first pressure within the third chamber is attained.

4. The volumetric infusion pump of claim 3 and further comprising:
   a second fixed contact located at a fixed position with respect to the third chamber, wherein the movable electric contact engages the second fixed contact when a second pressure within the third chamber is attained.

5. The volumetric infusion pump of claim 4 and further comprising:
   adjusting means for adjusting the fixed positions of the first and second fixed contacts.

6. A volumetric infusion pump for pumping fluid from a source to a patient, the pump comprising:
   pump housing means;
   a sealed integral disposable unit, which is supported by the pump housing means during operation of the pump, comprising:
   an inlet for receiving fluid from the the source;
   an outlet for supplying fluid under pressure to the patient;
   a sealed main flow passage between the inlet and the outlet;

flexible rolling diaphragm pumping chamber means connected to the main flow passage for pumping fluid from the inlet to the outlet;

a flexible pressure sensing chamber connected to the main flow passage between the flexible rolling diaphragm pumping chamber means and the outlet, the flexible pressure sensing chamber having a flexible rolling diaphragm which is movable as a function of fluid pressure within the flexible rolling diaphragm pumping chamber means;

piston means supported by the pump housing means for engaging the flexible rolling diaphragm means when the sealed integral disposable unit is supported by the pump housing means during operation of the pump;

pump drive means supported by the pump housing means for moving the piston means to cause the rolling diaphragm pumping chamber means to pump fluid from the inlet to the outlet;

valve means for controlling fluid flow through the main flow passage between the flexible rolling diaphragm pumping chamber means and the flexible pressure sensing chamber; and means supported by the pump housing means external to the flexible pressure sensing chamber and responsive to movement of the flexible diaphragm for providing an output which is a function of fluid pressure within the pressure sensing chamber, so that fluid is pumped from the inlet to the outlet without physically contacting the pump housing means, the pump drive means, or the means external to the pressure sensing chamber.

7. The invention of claim 6 wherein the means external to the pressure sensing chamber comprises:
   a cylinder for receiving the flexible rolling diaphragm pressure sensing chamber; and
   a piston movable within the cylinder in response to fluid pressure within the flexible rolling diaphragm pressure sensing chamber.

8. The invention of claim 7 wherein the means external to the pressure sensing chamber further comprises:
   a movable electric contact connected to and movable with the piston;
   a first fixed contact located at a fixed position with respect to the cylinder; and
   spring means for applying a spring force to the piston in a direction opposite the force supplied by fluid pressure within the flexible rolling diaphragm pressure sensing chamber.

9. The invention of claim 8 wherein the movable electric contact breaks contact with the first fixed contact when a first pressure within the flexible rolling diaphragm pressure sensing chamber is attained.

10. The invention of claim 9 and further comprising:
    a second fixed contact located at a fixed position with respect to the cylinder, wherein the movable electric contact engages the second fixed contact when a second pressure within the flexible rolling diaphragm pressure sensing chamber is attained.

11. The invention of claim 9 and further comprising:
    adjusting means for adjusting the fixed positions of the first and second fixed contacts.

* * * * *